United States Patent [19]

Keith et al.

[11] Patent Number: 5,015,231
[45] Date of Patent: May 14, 1991

[54] MULTIPART SPLIT SLEEVE BALLOON PROTECTOR FOR DILATATION CATHETER

[75] Inventors: Peter T. Keith, Edina; Charles L. Euteneuer, St. Michael, both of Minn.

[73] Assignee: SciMed Life Systems, Inc., Maple Grove, Minn.

[21] Appl. No.: 341,931

[22] Filed: Apr. 21, 1989

[51] Int. Cl.⁵ ............................................. A61M 29/00
[52] U.S. Cl. ...................................... 604/96; 604/103
[58] Field of Search ............................... 604/96–103, 604/192; 206/363–365; 24/136 L; 403/290

[56] References Cited

U.S. PATENT DOCUMENTS

| | | |
|---|---|---|
| 2,486,056 | 10/1949 | Oclassen . |
| 3,409,016 | 11/1968 | Foley . |
| 3,822,593 | 7/1974 | Oudewaal ............................. 73/343 |
| 4,248,246 | 2/1981 | Ikeda . |
| 4,275,591 | 6/1981 | Wand ................................. 73/864 |
| 4,416,267 | 11/1983 | Garren et al. ........................ 604/192 |
| 4,449,532 | 5/1984 | Storz . |
| 4,573,470 | 3/1986 | Samson et al. . |
| 4,592,744 | 6/1986 | Jagger et al. ........................ 604/192 |
| 4,636,201 | 1/1987 | Ambrose et al. ..................... 604/192 |
| 4,762,125 | 8/1988 | Lerman et al. ....................... 604/96 |
| 4,771,776 | 9/1988 | Powell et al. . |
| 4,846,344 | 7/1989 | Bala ................................... 206/306 |
| 4,846,801 | 7/1989 | Okuda et al. ........................ 604/218 |
| 4,921,483 | 5/1990 | Wijay et al. .......................... 604/96 |

Primary Examiner—Stephen C. Pellegrino
Assistant Examiner—Michael Rafa
Attorney, Agent, or Firm—Kinney & Lange

[57] ABSTRACT

The balloon of an angioplasty dilatation balloon catheter is covered by inner and outer balloon protector sleeves. The inner balloon protector sleeve has an expansion slit to facilitate application over the balloon.

65 Claims, 2 Drawing Sheets

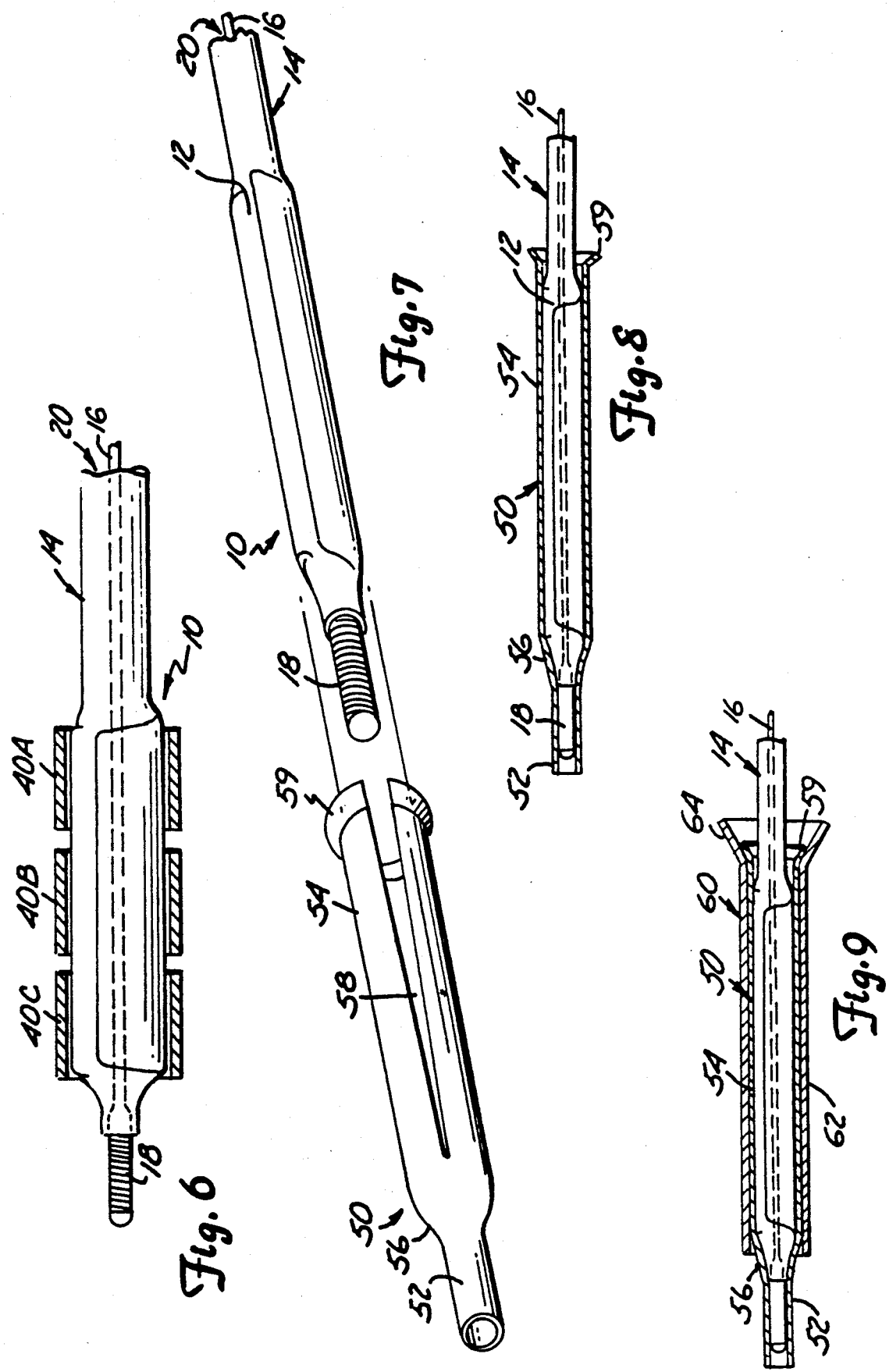

MULTIPART SPLIT SLEEVE BALLOON PROTECTOR FOR DILATATION CATHETER

REFERENCE TO COPENDING APPLICATION

Reference is hereby made to a copending application entitled "DILATATION CATHETER WITH TRIFOLD BALLOON" by C. Euteneuer which was filed on even date and which is assigned to the same assignee as the present application.

BACKGROUND OF THE INVENTION

1. Field of the Invention

The present invention relates to the field of angioplasty. In particular, the present invention relates to a balloon protector for a dilatation balloon catheter.

2. Description of the Prior Art

Angioplasty has gained wide acceptance in recent years as an efficient and effective method for opening stenoses in the coronary arteries and in other parts of the vascular system. The most widely used form of angioplasty makes use of a dilatation catheter which has an inflatable balloon at its distal end. Using fluoroscopy, the physician guides the catheter through the vascular system until the balloon is positioned across the stenosis. The balloon is then inflated by supplying a fluid under pressure through an inflation lumen to the balloon. The inflation of the balloon causes stretching of the artery and pressing of the lesion into the artery wall to reestablish acceptable blood flow through the artery.

One important characteristic of a dilatation balloon catheter used for angioplasty is its "profile", which is determined by the outer diameter of the distal end portion of the balloon when deflated. This outer diameter affects the ease and ability of the dilatation catheter to pass through a guide catheter, through the coronary arteries and across a tight lesion. Considerable effort has been spent in developing low profile dilatation balloon catheters by minimizing the dimensions of the core or inner tube which extends through the balloon to its distal end, and by reducing wall thicknesses, to the extent possible, of the balloon itself.

In order to reduce the outer diameter of the balloon catheter in its deflated condition, it is common to fold and/or wrap the flaps of the deflated balloon with a sleeve (or "balloon protector"). Prior to insertion of the catheter into the patient, the balloon protector is removed. When inflation fluid is applied to the deflated balloon, it causes the balloon flaps to unwrap so that the balloon can inflate to its full inflated state.

A balloon protector serves two important functions. First, it protects the balloon and the distal tip of the catheter from possible damage during shipping. Second, the balloon protector wraps the balloon tightly in its deflated condition to minimize the outer diameter of the balloon in its deflated state.

A balloon protector is typically applied to the distal end portion of the catheter prior to packaging and sterilization of the catheter. The sterilization process typically involves exposing the catheter, with the balloon protector in place, to an elevated temperature for a predetermined time period.

With certain balloon materials, such as polyolefin, the sterilization process will cause the balloon to be "heat set" in the folded or wrapped condition in which it is held by the balloon protector. As a result, when the balloon protector is later removed, the balloon remains in a tightly wrapped condition. This heat set of the balloon has a further advantage in that when the balloon is inflated and is then deflated, the application of a negative fluid pressure during deflation will cause the balloon to tend to return to its heat set tightly wrapped shape. This greatly facilitates the removing of the catheter after the dilatation procedure has been performed as well as the crossing of additional lesions using same catheter.

As angioplasty catheter distal sections (including the balloon) have become smaller, and more fragile, it has become increasingly difficult to apply a balloon protector which does not damage the catheter or the balloon and yet wraps the balloon as tightly as possible. There is a continuing need for improved balloon protectors for dilatation balloon catheters.

SUMMARY OF THE INVENTION

The present invention is a multipart balloon protector which includes a first inner balloon protector sleeve which is applied over the deflated balloon and a second outer balloon protector sleeve which is applied over the inner sleeve. The inner balloon protector sleeve is constructed so as to be radially compressible. In one preferred embodiment of the present invention, the inner balloon protector sleeve comprises a tube adapted for receiving the balloon with an elongated expansion slit in the wall of the tube extending from the proximal end of the tube approximately the length of the balloon. As the inner balloon protector sleeve slides over the balloon, the inner sleeve expands as the expansion slit separates to facilitate installation of the sleeve without needing excessive axial force. The second outer balloon protector sleeve then is applied over the inner balloon protector. The outer balloon protector sleeve compresses the inner balloon protector, closing the gap formed by the expansion slit. With the balloon being compressed by the two balloon protector sleeves, the catheter is then sterilized at an elevated temperature. As a result, the heat treatment step causes the deflated balloon to be compressed and therefore have a smaller outer diameter. When a balloon material is used which exhibits heat set characteristics, the deflated balloon will remain tightly compressed even after removal of the outer and inner balloon protector sleeves just prior to use.

The process may be repeated with progressively tighter-fitting inner and outer balloon protector sleeves followed by further heat treatment. These steps are repeated until the desired profile of the balloon is achieved. Ultimately, the balloon will be wrapped to the point where no interstitial space exists. At this point, further reduction of wrapped profile is impossible.

BRIEF DESCRIPTION OF THE DRAWINGS

FIGS. 1-9 show steps for folding the balloon of a dilatation balloon catheter and for applying the two-piece balloon protector of the present invention.

DETAILED DESCRIPTION OF THE PREFERRED EMBODIMENTS

Figure 1:
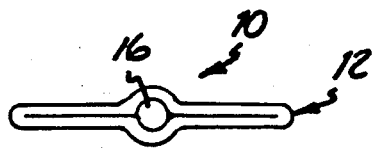

In the particular embodiment of the present invention illustrated in FIGS. 1-9, dilatation balloon catheter 10 is a "fixed wire" type of balloon catheter having an inflatable balloon 12 mounted at the distal end of hollow flexible shaft 14. Core member 16 extends through the interior of balloon 12 and has a spring coil tip 18 at its distal end. The distal end of balloon 12 is bonded to core 16. Inflation lumen 20 extends through the interior of shaft 14 and communicates with the interior of balloon 12. The proximal end of shaft 14, which is not shown, is preferably connected to a manifold, which in turn is capable of connection to an inflation device so that fluid pressure can be applied through inflation lumen 20 to the interior of balloon 12. By applying positive fluid pressure, balloon 12 is inflated. By applying negative fluid pressure (for example, by drawing a vacuum at the proximal end of lumen 20), balloon 12 is collapsed to its deflated condition.

In the particular embodiment shown in FIGS. 1-9, the balloon protector of the present invention is used in conjunction with a balloon 12 which, in its deflated state, has 3 wings or flaps 12A, 12B, and 12C. The advantages of this trifold balloon configuration is described in further detail in the above-mentioned copending application entitled "Dilatation Catheter With Trifold Balloon," and that description is incorporated by reference. The use of a trifold balloon, while offering significant advantages, is not crucial to the balloon protector of the present invention, which is equally applicable to balloons having other deflated shapes. However, a trifold balloon (FIGS. 1-4) coupled with an "initializing wrap and heat set" (FIGS. 5 and 6) facilitates advancement of the small inner and outer balloon protectors (FIGS. 7-9) of the present invention.

FIGS. 1-4 illustrate the formation of the trifold balloon configuration. In FIG. 1 balloon 12 is collapsed by the application of a vacuum to inflation lumen 20 so that a flat winged configuration is produced. Core 16 is in the center of the flat winged configuration shown in FIG. 1.

Figure 2:
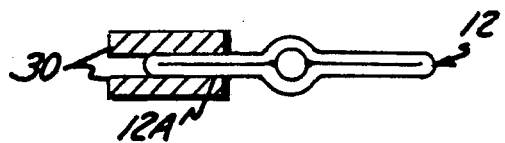

In FIG. 2, clamping fixture 30 is used to clamp approximately one-third of the distance across balloon 12. Clamp 30 is made of a material which will not tear, puncture or otherwise damage balloon 12.

Figure 3:
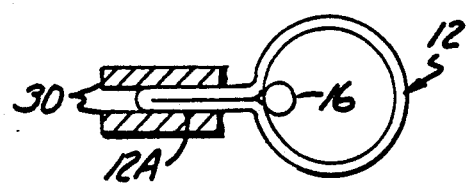

As illustrated in FIG. 3, balloon 12 is then inflated at low pressure while clamp 30 holds wing 12A. The unclamped portion of balloon 12, therefore, is reinflated.

Figure 4:
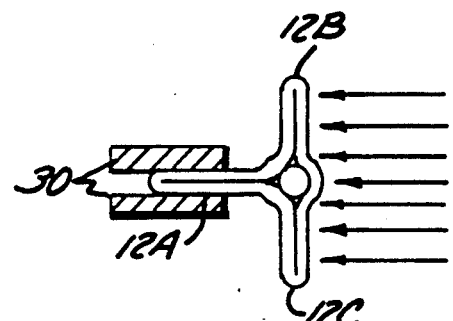

In FIG. 4, pressure is applied to the exterior of unclamped portion of balloon 12 while pulling a vacuum through inflation lumen 20, so that the unclamped portion of balloon 12 is deflated while being pressed against the side of clamp 30. This forms wings 12B and 12C. The result is a three wing configuration which generally has a T-shaped cross-section as shown in FIG. 4.

Figure 5:
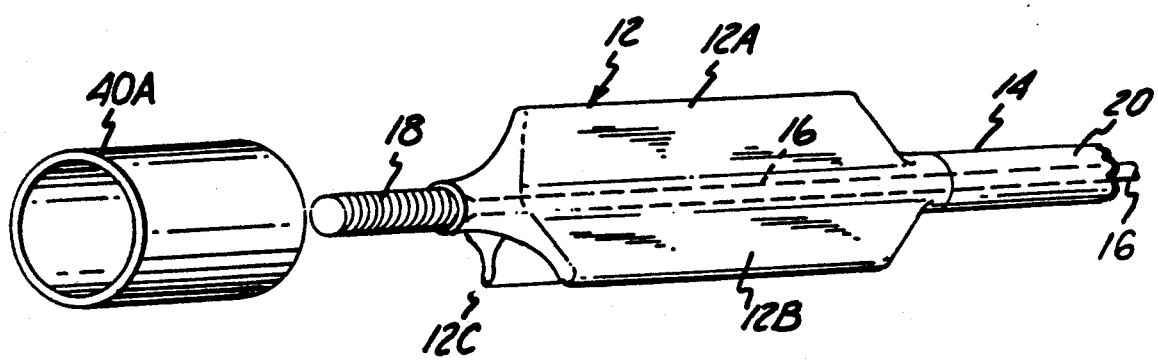

As shown in FIGS. 5 and 6, three relatively large inside diameter tube segments 40A-40C are advanced, one at a time from the distal end of catheter 10 over balloon 12. These tube segments 40A-40C initiate wrapping of the three wings or flaps 12A-12C of balloon 12. The inside diameters of tube segments 40A-40C are just large enough to ensure the core 16 will not buckle as tube segments 40A-40C are advanced over balloon 12. Using multiple segments 40A-40C reduces the frictional force build up which would occur if a single tube having a length equal to the total length of balloon 12 were applied. In addition, this allows the first segment 40A, once it is near the middle of balloon 12, to be pulled rather than pushed over the proximal balloon cone.

Once segments 40A-40C are in place and balloon 12 is partially folded as shown in FIG. 6, catheter 10 is subjected to an initial heat treatment at approximately 50° C. to heat set balloon 12. After the initial heat treatment, tube segments 40A-40C are removed from balloon 12. The initial heat treatment has caused the wings 12A-12C to fold or wrap further around core 16, so that balloon 12 is more tightly wrapped than it was prior to the initial heat treatment. This initial wrapping and setting facilitates ease of installation of the final protectors.

As shown in FIG. 7, the next step involves applying inner balloon protector sleeve 50 over the distal end of catheter 10. Inner balloon protector sleeve 50, is shown in FIG. 7, includes a narrow distal portion 52 and a wider proximal portion 54, with shoulder 56 connecting distal portion 52 to proximal portion 54.

Distal portion 52 of inner balloon protector sleeve 50 has an inner diameter which is slightly larger than the outer diameter of tip 18 of catheter 10. The length of distal portion 52 is approximately equal to the length by which tip 18 extends distally from the distal end of balloon 12.

Proximal portion 54 of inner balloon protector sleeve 50 has a length which is approximately equal to the length of balloon 12 and has a longitudinally extending expansion slit 58 which extends from the proximal end of inner balloon protector sleeve 50 substantially the entire length of proximal section 54. Inner balloon protector 50 also has a flange or flare 59 at its proximal end to reduce abruptness of the leading edge of inner protector 50 as it is urged onto balloon 12. The inner diameter of proximal section 54, when expansion slit 58 is closed, is slightly larger than the minimum profile diameter achievable for balloon 12 in its deflated condition.

Inner balloon protector sleeve 50 is applied over balloon 12 of catheter 10 by moving sleeve 50 in a proximal direction, starting at tip 18 at the distal end of catheter 10, while a vacuum is applied to balloon 12 through lumen 20. Sleeve 50 is gently urged over balloon 12 as sleeve 50 is moved in a proximal direction relative to catheter 10. Sleeve 50 must be aligned so that none of the wings 12A-12C project out of sleeve 50 through slit 58. Expansion slit 58 provides proximal sleeve portion 54 with a variable inner diameter, which reduces the force required to apply sleeve 50 onto balloon 12 by reducing friction between balloon 12 and the inner wall of sleeve 50. This ensures that balloon 12 will not be torn and that core 16 will not be crushed or bent during application of sleeve 50.

FIG. 9 shows the next step in which outer balloon protector sleeve 60 is applied over inner balloon protector sleeve 50. Sleeve 60 slides over narrow distal section 52 of inner balloon protector sleeve 50 and then over the wider proximal section 54 of sleeve 50 until it reaches the position shown in FIG. 9.

Outer balloon protector sleeve 60 has a main tubular body portion 62 and a flange or lip section 64 at its proximal end. The inner diameter of outer balloon protector sleeve 60 is about 0.001 inch smaller than the outer diameter of the inner balloon protector proximal section 54. This causes expansion slit 58 to be closed when outer balloon protector sleeve 60 is applied over inner balloon protector sleeve 50, as well as overall compression of inner balloon protector sleeve 50.

As outer balloon protector sleeve 60 is applied over inner balloon protector sleeve 50, the narrow distal section 52 of inner balloon protector sleeve 50 may be grasped such that force due to friction during application is transferred between outer and inner balloon protector sleeves 60 and 50 and not to any portion of balloon catheter 10. As expansion slit 58 is closed and forced together by outer balloon protector sleeve 60, balloon flaps 12A-12C become more tightly wrapped.

After both sleeves 50 and 60 are in place over the distal end portion of catheter 10, a heated sterilization cycle is performed. This causes balloon 12 to be heat set in its further definitive compressed form. The heat setting of balloon 12 provides a "memory" to balloon 12 so that when inner and outer balloon protector sleeves 50 and 60 are removed prior to use, balloon 12 will remain in its tightly-wrapped, compressed form. Even after balloon 12 has been inflated, when it is again deflated it will tend to return to substantially the same shape that it had during the heat sterilization process. Therefore, small profiles can be achieved even after balloon inflation.

In a preferred embodiment of the present invention, inner and outer sleeves 50 and 60 are a heat shrinkable material which also will not stick to catheter 10 (and particularly to balloon 12). One preferred material for segments 40A-40C, and inner and outer protector sleeves 50 and 60 is polytetrafluoroethylene.

The outer diameter of balloon 12 may be further reduced if necessary. Inner and outer sleeves 50 and 60 are removed after an elevated temperature heat setting step, and a new set of inner and outer sleeves are then applied over balloon 12. The new balloon protector sleeves are of similar construction but have smaller diameters than those of the original sleeves. By repeating the steps of applying the balloon protector sleeves and performing a heat setting step, while using successively smaller and smaller sets of inner and outer sleeves, balloon 12 is treated until it reaches the desired profile, or the minimum achievable profile is achieved.

A major advantage of the slit inner and compression fit outer sleeve protector of the invention is that the minimum achievable profile can be achieved with one regular heat setting and "prewrapping" operation, followed by the inner and outer balloon protector installation. This allows substantial reductions in profile of the balloon with minimal operations and without damaging the balloon.

In conclusion, the present invention is an improved balloon protector which is effective in creating a tightly-wrapped balloon configuration without tearing or otherwise damaging the balloon and without bending or collapsing the core of the balloon catheter.

Although the present invention has been described with reference to preferred embodiments, workers skilled in the art will recognize the changes that may be made in form and detail without departing from the spirit and scope of the invention. For example, the present invention is applicable to both over-the-wire and fixed-wire types of balloon catheters.

We claim:

1. A balloon protector for a balloon catheter having a balloon positioned adjacent a distal end, the balloon protector comprising:
   an inner sleeve having an interior for receiving the balloon; and
   an outer sleeve having an interior for receiving the inner sleeve, the interior of the outer sleeve being sized smaller than an exterior of the inner sleeve, such that the outer sleeve applies a radially inward compressive force to the inner sleeve and the balloon when the outer sleeve is applied over the inner sleeve.

2. The balloon protector of claim 1 wherein the inner sleeve includes an elongated slit therein.

3. The balloon protector of claim 2 wherein the elongated slit extends in a generally longitudinal direction.

4. The balloon protector of claim 3 wherein the slit extends distally from a proximal end of the inner sleeve.

5. The balloon protector of claim 5 wherein the inner sleeve has a distal portion having a first inner diameter and a proximal portion having a second, larger inner diameter.

6. The balloon protector of claim 3 wherein the outer sleeve has an inner diameter which is less than an outer diameter of the inner sleeve and thereby causes the slit to close when the outer sleeve is applied over the inner sleeve.

7. The balloon protector of claim 1 wherein the inner sleeve includes an outwardly projecting portion at a proximal end that reduces the abruptness of a leading edge of the inner sleeve as the inner sleeve receives the balloon.

8. The balloon protector of claim 1 wherein the inner sleeve includes a distal neck portion for receiving force as the outer sleeve is applied over the inner sleeve.

9. The balloon protector of claim 1 wherein the inner sleeve includes a distal portion adapted for receiving a flexible distal tip portion of the balloon catheter and a proximal portion for receiving and surrounding the balloon.

10. The balloon protector of claim 1 wherein a proximal end of the outer sleeve includes a lip portion that reduces the abruptness of a leading edge of the outer sleeve as the outer sleeve receives the inner sleeve.

11. The balloon protector of claim 1 wherein the inner sleeve and the outer sleeve are formed of material having a heat-shrink characteristic.

12. The balloon protector of claim 1 wherein the inner sleeve and the outer sleeve are polytetraflouroethylene.

13. A balloon protector for a balloon catheter having a balloon positioned adjacent a distal end, the balloon protector comprising:
   an inner sleeve having an interior for receiving the balloon;
   an outer sleeve having an interior for receiving the inner sleeve; and
   means extending along a wall of the inner sleeve for allowing a varying of a radial dimension of the inner sleeve during application of the inner sleeve over the balloon and during application of the outer sleeve over the inner sleeve.

14. A balloon protector for a balloon catheter having a balloon positioned adjacent a distal end, the balloon protector comprising:
   an inner sleeve for engaging and covering the balloon while the balloon is in a deflated state; and
   an outer sleeve for surrounding and engaging the inner sleeve to hold the inner sleeve in position over the balloon, the outer sleeve having an inner diameter that is less than an outer diameter of the inner sleeve such that the outer sleeve applies a radially inward compressive force on the inner sleeve and the balloon.

15. The balloon protector of claim 14 wherein the inner sleeve includes means for expanding in a radial direction during application of the inner sleeve over the balloon.

16. The balloon protector of claim 15 wherein the means for expanding includes a generally longitudinally extending slit in the inner sleeve.

17. The balloon protector of claim 16 wherein the outer sleeve has an inner dimension which causes the slit to close as the outer sleeve is applied over the inner sleeve.

18. A balloon protector for a balloon catheter having a balloon positioned adjacent a distal end, the balloon protector comprising:
an inner sleeve having an interior for receiving the balloon, the inner sleeve having an elongated slit therein which extends in a generally longitudinal direction; and
an outer sleeve having an interior for receiving the inner sleeve.

19. The balloon protector of claim 18 wherein the slit extends distally from a proximal end of the inner sleeve.

20. The balloon protector of claim 19 wherein the inner sleeve has a distal portion having a first inner diameter and a proximal portion having a second, larger inner diameter.

21. The balloon protector of claim 18 wherein the outer sleeve has an inner diameter which causes the slit to close when the outer sleeve is applied over the inner sleeve.

22. The balloon protector of claim 18 wherein the inner sleeve includes a distal neck portion for receiving force as the outer sleeve is applied over the inner sleeve.

23. The balloon protector of claim 18 wherein the inner sleeve includes a distal portion adapted for receiving a flexible distal tip portion of the balloon catheter and a proximal portion for receiving and surrounding the balloon.

24. The balloon protector of claim 18 wherein the inner sleeve and the outer sleeve are formed of material having a heat-shrink characteristic.

25. A balloon protector for a balloon catheter having a balloon positioned adjacent a distal end, the balloon protector comprising:
an inner sleeve for covering the balloon, wherein the inner sleeve includes means for expanding in a radial direction during application of the inner sleeve over the balloon; and
an outer sleeve for surrounding the inner sleeve to hold the inner sleeve in position over the balloon.

26. The balloon protector of claim 25 wherein the means for expanding includes a generally longitudinally extending slit in the inner space.

27. The balloon protector of claim 26 wherein the outer sleeve has an inner dimension which causes the slit to close as the outer sleeve is applied over the inner sleeve.

28. In combination:
a balloon catheter having an inflatable balloon positioned adjacent a distal end; and
a balloon protector positioned over the balloon to protect the balloon and hold the balloon in a deflated condition, the balloon protector including:
an inner sleeve positioned over at least a portion of the balloon, wherein the inner sleeve includes means for expanding a radial dimension of the inner sleeve during application of the inner sleeve over the balloon; and
an outer sleeve positioned over the inner sleeve, the outer sleeve being sized to apply a radially inward compressive force to the inner sleeve and the balloon.

29. The combination of claim 28 wherein the inner sleeve includes means for expanding a radial dimension of the inner sleeve during application of the inner sleeve over the balloon.

30. The combination of claim 29 wherein the means for expanding includes a generally longitudinally extending slit in the inner sleeve.

31. The combination of claim 30 wherein the outer sleeve has an inner dimension which causes the slit to close as the outer sleeve is applied over the inner sleeve.

32. The combination of claim 28 wherein the balloon catheter has a distal tip portion which extends distally of the balloon, and wherein the inner sleeve includes a distal portion for covering the distal tip portion of the catheter and a proximal portion for covering the balloon.

33. The combination of claim 32 wherein the outer sleeve is shorter than the inner sleeve.

34. The combination of claim 33 wherein the outer sleeve has an outwardly projecting portion for facilitating gripping of the outer sleeve as the outer sleeve is pulled onto the inner sleeve.

35. The combination of claim 34 wherein the outwardly projecting portion is a lip positioned at a proximal end of the outer sleeve.

36. The combination of claim 32 wherein the inner sleeve includes a generally longitudinal slit in the proximal portion extending from a proximal end of the inner sleeve.

37. The combination of claim 28 wherein the inner and outer sleeves are polytetrafloureothylene.

38. The combination of claim 28 wherein the inner and outer sleeves have been heat-shrunk in position over the balloon.

39. In combination:
a balloon catheter having an inflatable balloon positioned adjacent a distal end; and
a balloon protector positioned over the balloon to protect the balloon and hold the balloon in a deflated condition, the balloon protector including:
an inner sleeve positioned over at least a portion of the balloon, wherein the inner sleeve includes means for expanding a radial dimension of the inner sleeve during application of the inner sleeve over the balloon; and
an outer sleeve positioned over the inner sleeve.

40. The combination of claim 39 wherein the means for expanding includes a generally longitudinally extending slit in the inner sleeve.

41. The combination of claim 40 wherein the outer sleeve has an inner dimension which causes the slit to close as the outer sleeve is applied over the inner sleeve.

42. In combination:
a balloon catheter having an inflatable balloon positioned adjacent a distal end; and
a balloon protector positioned over the balloon to protect the balloon and hold the balloon in a deflated condition, the balloon protector including:
an inner sleeve positioned over at least a portion of the balloon wherein the balloon catheter has a distal tip portion which extends distally of the balloon, and wherein the inner sleeve includes a distal portion for covering the distal tip portion of the catheter and a proximal portion for covering the balloon; and
an outer sleeve positioned over the inner sleeve.

43. The combination of claim 42 wherein the outer sleeve is shorter than the inner sleeve.

44. The combination of claim 43 wherein the outer sleeve has an outwardly projecting portion for facilitating gripping of the outer sleeve as the outer sleeve is pulled onto the inner sleeve.

45. The combination of claim 44 wherein the outwardly projecting portion is a lip positioned at a proximal end of the outer sleeve.

46. The combination of claim 42 wherein the inner sleeve includes a generally longitudinal slit in the proximal portion extending from a proximal end of the inner sleeve.

47. The combination of claim 42 wherein the inner and outer sleeves are polytetraflouroethylene.

48. The combination of claim 42 wherein the inner and outer sleeves have been heat-shrunk in portion over the balloon.

49. A method of forming a balloon protector over a balloon positioned adjacent a distal end of a balloon catheter, the method comprising:
    covering at least a portion of the balloon with an inner sleeve; and
    covering the inner sleeve with an outer sleeve which has an interior sized smaller than an exterior of the inner sleeve, such that the outer sleeve applies a radially inward compressive force on the inner sleeve and the balloon.

50. The method of claim 49 and further comprising:
    exposing the balloon, the inner sleeve, and the outer sleeve to an elevated temperature to cause the inner and outer sleeves to shrink around the balloon.

51. The method of claim 49 wherein the inner sleeve includes a distal neck portion, and covering the inner sleeve includes grasping the neck portion while sliding the outer sleeve over the inner sleeve.

52. The method of claim 49 wherein covering the balloon with the inner sleeve includes sliding the inner sleeve over the balloon in a distal-to-proximal direction.

53. The method of claim 49 wherein the inner sleeve has a generally longitudinally extending slit.

54. The method of claim 49 and further comprising:
    preparing the balloon for covering with the inner sleeve by forming a plurality of flaps and wrapping the flaps around the catheter.

55. A method of forming a balloon protector over a balloon positioned adjacent a distal end of a balloon catheter, the method comprising:
    covering at least a portion of the balloon with an inner sleeve;
    covering the inner sleeve with an outer sleeve; and
    exposing the balloon, the inner sleeve, and the outer sleeve to an elevated temperature to cause the inner and outer sleeves to shrink around the balloon.

56. The method of claim 55 wherein the inner sleeve has a generally longitudinally extending slit.

57. The method of claim 55 and further comprising:
    preparing the balloon for covering with the inner sleeve by forming a plurality of flaps and wrapping the flaps around the catheter.

58. A method of forming a balloon protector over a balloon positioned adjacent a distal end of a balloon catheter, the method comprising:
    covering at least a portion of the balloon with an inner sleeve, wherein the inner sleeve includes a distal neck portion, and covering the inner sleeve includes grasping the neck portion while sliding the outer sleeve over the inner sleeve; and
    covering the inner sleeve with an outer sleeve.

59. The method of claim 58 wherein covering the balloon with the inner sleeve includes sliding the inner sleeve over the balloon in a distal-to-proximal direction.

60. The method of claim 58 wherein the inner sleeve has a generally longitudinally extending slit.

61. The method of claim 58 and further comprising:
    preparing the balloon for covering with the inner sleeve by forming a plurality of flaps and wrapping the flaps around the catheter.

62. A method of forming a balloon protector over a balloon positioned adjacent a distal end of a balloon catheter, the method comprising:
    covering at least a portion of the balloon with an inner sleeve which has a generally longitudinally extending slit; and
    covering the inner sleeve with an outer sleeve.

63. The method of claim 62 wherein the inner sleeve includes a distal neck portion, and covering the inner sleeve includes grasping the neck portion while sliding the outer sleeve over the inner sleeve.

64. The method of claim 62 wherein covering the balloon with the inner sleeve includes sliding the inner sleeve over the balloon in a distal-to-proximal direction.

65. A method of forming a balloon protector over a deflated balloon positioned adjacent a distal end of a balloon catheter, the method comprising:
    preparing the deflated balloon by forming a plurality of flaps and wrapping the flaps around the catheter;
    covering at least a portion of the balloon with an inner sleeve which engages the balloon; and
    covering the inner sleeve with an outer sleeve which engages the inner sleeve.

* * * * *